(12) United States Patent
Asirvatham et al.

(10) Patent No.: US 12,336,770 B2
(45) Date of Patent: *Jun. 24, 2025

(54) ENDOSCOPIC ULTRASOUND ELECTROPORATION

(71) Applicant: Mayo Foundation for Medical Education and Research, Rochester, MN (US)

(72) Inventors: Samuel J. Asirvatham, Rochester, MN (US); Barham K. Abu Dayyeh, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/142,385

(22) Filed: May 2, 2023

(65) Prior Publication Data

US 2023/0263578 A1 Aug. 24, 2023

Related U.S. Application Data

(63) Continuation of application No. 16/644,785, filed as application No. PCT/US2018/049682 on Sep. 6, 2018, now Pat. No. 11,672,608.

(Continued)

(51) Int. Cl.
*A61B 34/20* (2016.01)
*A61B 1/015* (2006.01)
(Continued)

(52) U.S. Cl.
CPC .............. *A61B 34/20* (2016.02); *A61B 1/015* (2013.01); *A61B 8/0841* (2013.01); *A61B 8/12* (2013.01);
(Continued)

(58) Field of Classification Search
CPC ......... A61B 1/015; A61B 1/018; A61B 18/00; A61B 18/06; A61B 18/1492; A61B 18/18; A61B 2018/0022; A61B 2018/00267; A61B 2018/00577; A61B 2018/00613; A61B 2018/00642; A61B 2018/00738; A61B 2018/00761; A61B 2018/00863; A61B 2018/00875; A61B 2018/00982;
(Continued)

(56) References Cited

U.S. PATENT DOCUMENTS 6,142,945 A * 11/2000 Sakamoto .............. A61B 8/445
600/459
11,672,608 B2 * 6/2023 Asirvatham ........... A61B 18/00
600/424

(Continued)

OTHER PUBLICATIONS

Han et al., "Endoscopic Ultrasound-Guided Direct Intervention for Solid Pancreatic Tumors," Clin. Endosc., 50(2):126-137, Mar. 2017.
(Continued)

*Primary Examiner* — Michael T Rozanski
(74) *Attorney, Agent, or Firm* — Fish & Richardson P.C.

(57) ABSTRACT

Cystic lesions can be treated by electroporation. For example, this document describes methods and devices for endoscopic ultrasound-guided ablation of cystic lesions using a needle for electroporation.

16 Claims, 3 Drawing Sheets

Related U.S. Application Data

(60) Provisional application No. 62/554,859, filed on Sep. 6, 2017.

(51) Int. Cl.
| | | |
|---|---|---|
| *A61B 8/00* | (2006.01) | |
| *A61B 8/08* | (2006.01) | |
| *A61B 8/12* | (2006.01) | |
| *A61B 18/00* | (2006.01) | |
| *A61B 18/06* | (2006.01) | |
| *A61B 18/18* | (2006.01) | |
| *A61N 1/32* | (2006.01) | |
| *A61N 5/06* | (2006.01) | |

(52) U.S. Cl.
CPC .............. *A61B 8/445* (2013.01); *A61B 18/00* (2013.01); *A61B 18/06* (2013.01); *A61B 18/18* (2013.01); *A61N 1/327* (2013.01); *A61N 5/062* (2013.01); *A61B 2018/0022* (2013.01); *A61B 2018/00577* (2013.01); *A61B 2018/00613* (2013.01); *A61B 2018/00982* (2013.01); *A61B 2018/1807* (2013.01); *A61B 2034/2063* (2016.02)

(58) Field of Classification Search
CPC .... A61B 2018/1425; A61B 2018/1807; A61B 2034/2063; A61B 2218/002; A61B 2218/007; A61B 34/20; A61B 8/0841; A61B 8/12; A61B 8/445; A61N 1/327; A61N 5/062

See application file for complete search history.

(56) References Cited

U.S. PATENT DOCUMENTS

| | | | |
|---|---|---|---|
| 2004/0204669 A1 | 10/2004 | Hofmann | |
| 2008/0051626 A1 | 2/2008 | Sato et al. | |
| 2011/0160514 A1* | 6/2011 | Long | A61B 18/1477 606/41 |
| 2011/0282138 A1* | 11/2011 | Nakajima | A61B 17/3403 600/104 |
| 2015/0374435 A1 | 12/2015 | Cao et al. | |
| 2016/0058502 A1 | 3/2016 | Clark et al. | |
| 2016/0113709 A1* | 4/2016 | Maor | A61B 18/1492 606/41 |
| 2016/0192911 A1 | 7/2016 | Kassab et al. | |
| 2016/0296280 A1 | 10/2016 | Long | |
| 2017/0014596 A1* | 1/2017 | Rajagopalan | A61B 18/02 |
| 2017/0042614 A1* | 2/2017 | Salahieh | A61B 1/00082 |
| 2017/0105793 A1 | 4/2017 | Cao et al. | |
| 2017/0215952 A1 | 8/2017 | Nair | |
| 2018/0303543 A1* | 10/2018 | Stewart | A61B 18/1492 |
| 2021/0059759 A1 | 3/2021 | Asirvatham et al. | |

OTHER PUBLICATIONS

International Preliminary Report on Patentability International Application No. PCT/US2018/049682 dated Mar. 19, 2020, 9 pages.
International Search Report & Written Opinion in International Application No. PCT/US2018/049682 dated Oct. 26, 2018, 22 pages.
Lakhtakia et al., "EUS-guided radiofrequency ablation for management of pancreatic insulinoma by using a novel needle electrode (with videos)," Gastrointest Endosc., 83(1):234-239, Jan. 2016.
Rombouts et al., "Irreversible Electroporation of the Pancreas Using Parallel Plate Electrodes in a Porcine Model: A Feasibility Study," PLOS One, 12(1):e0169396, Jan. 2017.

* cited by examiner

ENDOSCOPIC ULTRASOUND ELECTROPORATION

CROSS-REFERENCE TO RELATED APPLICATIONS

This application is a continuation of U.S. application Ser. No. 16/644,785, filed Mar. 5, 2020, which is a National Stage Application under 35 U.S.C. § 371 that claims the benefit of Application Serial No. PCT/US2018/049682, filed Sep. 6, 2018, which also claims the benefit of U.S. Provisional Application Ser. No. 62/554,859, filed Sep. 6, 2017. The disclosures of the prior applications are considered part of (and are incorporated by reference in) the disclosure of this application.

BACKGROUND

1. Technical Field

This document relates to methods and devices for treating cystic lesions. For example, this document relates to methods and devices for endoscopic ultrasound-guided ablation of cystic lesions using a needle to deliver non-thermal electroporation.

2. Background Information

Mucinous pancreas cystic lesions (mucinous cystic neoplasms [MCN] and side-branch intraductal papillary mucinous neoplasms [sb-IPMN]) are prevalent pre-neoplastic lesions of the pancreas that are often found incidentally on cross-sectional imaging. The rate of progression to pancreas cancer is variable and thus regular surveillance intervals are usually recommended to detect high risk features or changes within these cysts that usually necessitate invasive surgical resection.

Electroporation is a technique that uses high voltage rapid burst of current to non-thermally introduce multiple nano pores with the cells' walls of surrounding tissue. Depending on the voltage and frequency used these pores can be reversible (i.e., increase the permeability of these cell to chemotherapeutic agents) and or irreversible (i.e., trigger cell death by the process of apoptosis rather than necrosis).

SUMMARY

This document describes methods and devices for treating cystic lesions. For example, this document describes methods and devices for endoscopic ultrasound-guided ablation of cystic lesions using a needle to deliver non-thermal electroporation.

In one implementation, a method of performing electroporation includes inserting a needle into a working channel of an endoscope or an echoendoscope (forward or side-viewing), advancing the needle such that a distal end portion of the needle emerges from the working channel, inserting the distal end portion of the needle into a cyst using endoscopic ultrasound guidance, removing a first fluid from the cyst via a first aperture defined by the distal end portion of the needle, injecting a second fluid into the cyst via at least one of the first aperture and a second aperture defined by the distal end portion of the needle, and generating an electrical field via an electrode on the distal end portion of the needle, where the electrical field is conducted by the second fluid to cause non-thermal electroporation of cells of the cyst.

Such a method can optionally include one or more of the following features. The method can include inflating a balloon located on the distal end portion of the needle. One or more electrodes can be located on an outer surface of a wall of the balloon. The second aperture can be defined by a wall of the balloon. The balloon can be inflated using fluid or air. The outer balloon can include at least one of a flow monitor and a pressure monitor to regulate its inflation and pressure in relation to the cyst wall to enhance electrical conductivity and coupling and minimize trauma to the cyst wall. A second fluid can be injected to create a conductive area between the outer surface of the balloon wall and the second aperture or cyst wall. The method can include injecting a chemotherapeutic agent into the cyst via at least one of the first aperture or the second aperture, where the chemotherapeutic agent causes chemoelectroablation of the cyst.

In another implementation, an endoscopically-deliverable ultrasound-guided electroporation needle can include an elongate needle shaft configured for passing through a working channel of an endoscope, an aperture defined at a distal end portion of the needle shaft, and one or more electrodes located on the distal end portion of the needle shaft.

Such a needle can optionally include one or more of the following features. The aperture can allow for at least one of aspiration of a first fluid or injection of a second fluid through a lumen defined by the needle shaft. The needle can include a second aperture, where the second aperture allows for the other of aspiration of the first fluid or injection of the second fluid. The electrodes can allow an electrical field to be generated in the second fluid. The needle can include at least one of a flow monitor and a pressure monitor in communication with a lumen defined by the needle shaft.

In yet another implementation, an endoscopically-deliverable ultrasound-guided electroporation needle includes an elongate needle shaft configured for passing through a working channel of an endoscope, a first aperture located at a distal end portion of the needle shaft, and a balloon affixed on the distal end portion of the needle shaft, where the balloon can be inflated. The balloon can include an electrode coupled on an outer surface of a wall of the balloon, and a second aperture defined by the wall of the balloon.

Such a needle can optionally include one or more of the following features. The first aperture can allow aspiration of a first fluid. The second aperture can allow injection of a second fluid. Inflation of the balloon can be caused by injection of the second fluid. The electrode can allow an electrical field to be generated in the second fluid. The needle can include at least one of a flow monitor or a pressure monitor in communication with a lumen defined by the needle shaft to calculate volume aspirated and injected and prevent pressure build up within the cyst and trauma. In some cases, suction rather than balloon-based expansion can be applied to collapse the cyst wall around the electroporation balloon electrode and thin layer of conductive material can be applied to achieve the desired electroporation effect as stretch and suction can have independent membrane porating action that is independent of a DC field being created.

In yet another implementation, an endoscopically-deliverable ultrasound-guided electroporation needle can include an elongate needle shaft configured for passing through a working channel of an endoscope, a first aperture located at a distal portion of the needle shaft, and an electroporation basket affixed distal to the distal portion of the needle shaft, wherein the electroporation basket can be expanded. The electroporation basket can include an electrode coupled on an outer surface of an arm of the electroporation basket.

Such a needle can optionally include one or more of the following features. The first aperture can allow aspiration of a first fluid. The first aperture can allow injection of a second fluid. The electrode can allow an electrical field to be generated in the second fluid. The needle can further include at least one of a flow monitor or a pressure monitor in communication with a lumen defined by the needle shaft. A tip of the needle can be blunt and the needle can be configured to be delivered over a wire into a cystic structure. The needle shaft can include a sheath configured to removably cover the electroporation basket.

The conductive fluid injected can include, but is not limited to, various saline concentration and non-sodium based salt solutions such has calcium chloride. The conductive fluid injected can be of different viscosity and can include a radio-opaque or fluorescent marker, chemotherapeutic of ablative agent, or a photosensitizer agent delivered locally in small concentrations to the cyst wall via the process of electroporation and enhance the ablation ability using light.

In some cases, the range of voltage and pulse width can be specified for nanosecond pulse width delivery of high voltage impulses delivered in a bipolar fashion, that is, without a reference electrode or a surface patch. Bipolar stimulation may reduce stimulation of skeletal muscle, pain fibers, or autonomic nervous system. In some cases, monopolar, higher pulse width type stimulation can be delivered with a reference electrode or surface patch. In some cases, an automated closed loop feedback system can provide real time recordings of variably filtered high dynamic range signals of neural and smooth muscle electrograms so as to titrate the electroporation delivery and reduce collateral/unwanted electroporation effects in nontargeted tissue. In some cases, there can be situations where collateral effects are desired, for example, to ablate the celiac or superior mesenteric artery nerve plexus and or ganglia to induce reversible or irreversible non-thermal ablation of the plexus or ganglia for management of pain.

In some cases, the tip of the electroporation catheter can be blunt and delivered over a wire into a cystic structure such as the biliary tree using a duodenoscopy to administer reversible and or irreversible electroporation with or without chemoelectroablation.

Particular embodiments of the subject matter described in this document can be implemented to realize one or more of the following advantages. The shape of the electrical field can be closely regulated to control the treated area. The technique described provides contact with the cyst wall via a conductive medium rather than direct touch with an electrode allowing for non-thermal non-contact electroporation. Therefore, this ablative technique can provide an effective, efficient, and safe method of treating these cysts. This technique can have a very low risk of damage to the sensitive critical tissue surrounding the ablation, such as healthy pancreas and surrounding blood vessels. When using a balloon on a needle as described below, the balloon can be inflated to take the shape of the cyst for more efficient delivery of the current and to minimize the volume of conductive fluid injected.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, method and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers represent corresponding parts throughout.

DETAILED DESCRIPTION

This document describes methods and devices for treating cystic lesions. For example, this document describes methods and devices for endoscopic ultrasound-guided ablation of cystic lesions using a needle to deliver non-thermal electroporation.

Ablating cystic neoplastic lesions prior to progression to cancer has been a long desired goal of therapeutic endosonography (EUS). This goal has not consistently been attainable with current technology that delivers chemical ablation techniques (such as ethanol ablation) or heat delivery techniques (such as radio frequency ablation catheters). The reasons for failure of current techniques can be multifactorial, but include the lack of uniformity in delivering the ablative medium effectively and uniformly to the wall of the cystic lesion, as these technologies often require direct contact with the wall of the cyst, which can be asymmetric and lobulated in nature.

Using the methods and devices described herein, the shape of the electrical field can be closely regulated to control the treated area. Given the non-thermal non-contact (only requiring contact with the cyst wall via a conductive medium rather than direct touch with an electrode), the provided ablative techniques can be an effective, efficient, and safe ablative method of these cysts. This technique can be used while having only a very low risk of damage to the sensitive critical tissue surrounding the ablation, such as healthy pancreas and surrounding blood vessels. When using a balloon on the needle as described below, the balloon can be inflated to take the shape of the cyst for more efficient delivery of the current and to minimize the volume of conductive fluid injected. Suction can also be applied to maximize coupling and treatment effect.

Figure 1:
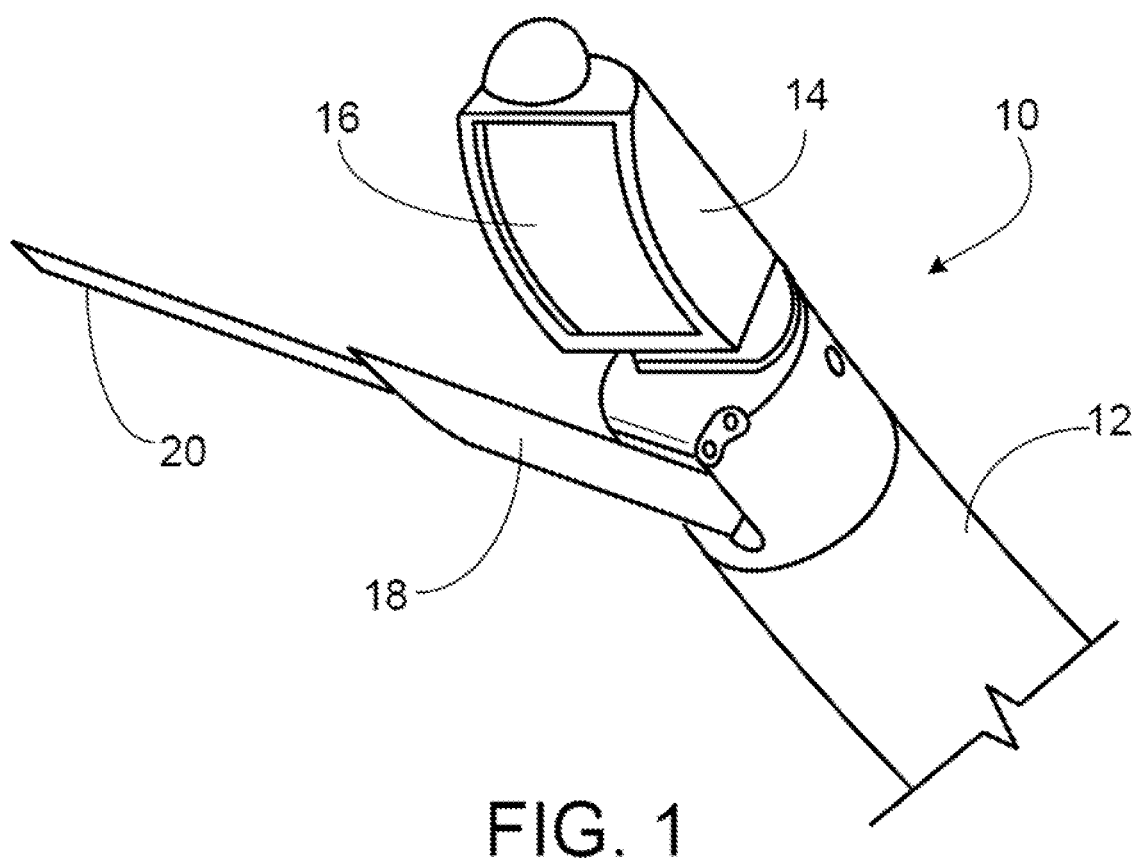
FIG. 1 is a perspective view of a distal end portion of an endoscopic ultrasound scope in accordance with some embodiments provided herein.

Referring to FIG. 1, an endoscopic ultrasound scope 10 can include an endoscope 12, an ultrasound head 14 and an instrument channel 18. In some cases, the ultrasound head 14 can include a transducer 16.

Endoscopic ultrasound scope 10 can include endoscope 12, which can enter into an orifice of a mammal (e.g., a human). In some cases, endoscopic ultrasound scope 10 can include, at a proximal end, a plurality of controls. The controls can include knobs, buttons, valves, switches, openings, channels, and/or locks. The controls can be used to adjust a direction of endoscope 12, lock a position of endoscope 12, enable/disable features of endoscope 12, and/or insert tools into endoscope 12.

Endoscope 12 can include ultrasound head 14 and instrument channel 18. In some cases, endoscope 12 can be flexible such that endoscope 12 can be maneuvered based on changes to the controls of endoscopic ultrasound scope 10. In some cases, endoscope 12 can include a bending section that can be maneuverable via the controls and an insertion tube section that can be flexible but does not have maneuverability capabilities. In some cases, endoscope 12 is made of suitable materials that are biocompatible. In some cases, endoscope 12 can have a suitable diameter, such as within a range from about 4 mm to about 15 mm, such that endoscope 12 can pass through a mouth, esophagus, stomach and/or duodenum of a patient.

Ultrasound head 14 can be located at a distal end of endoscope 12 and can include a transducer 16. In some cases, transducer 16 can be a linear transducer such that ultrasound images captured are parallel to endoscope 12. In some cases, transducer 16 can be a radial transducer such that ultrasound images captured are perpendicular to endoscope 12. In some cases, transducer 16 can be front viewing at the tip (rather than side) of endoscope 12. In some cases, ultrasound head 14 can include a camera such that a user can direct endoscope 12 to a desired location. In some cases, ultrasound head 14 can include a light source to aid in directing endoscope 12 to a desired location. In some cases, ultrasound head 14 can include other devices/features such as apertures, channels, or nozzles.

Instrument channel 18 can be coupled to an instrument channel located at a proximal end of endoscopic ultrasound scope 10 such that an instrument 18 inserted at the proximal end can exit from instrument channel 18 to interact with the biological material near the distal end of the endoscope 12. In some cases, instrument channel 18 can be a projection away from ultrasound head 14, as shown in FIG. 1. In some cases, a direction and/or angle of the instrument channel 18 can be modified by the controls of endoscopic ultrasound scope 10. In some cases, instrument channel 18 may be located on ultrasound head 14.

Figure 2:
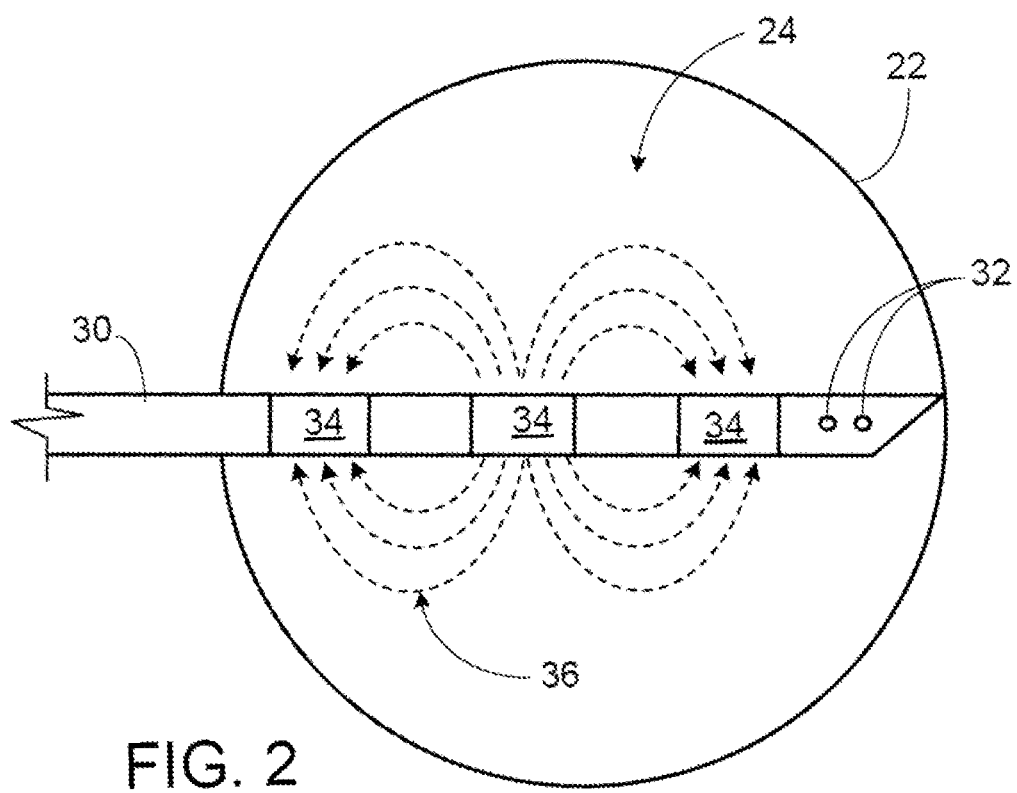
FIG. 2 is a schematic depiction of an endoscopic ultrasound needle in a cyst in accordance with some embodiments provided herein.

Referring to FIG. 2, an endoscopically-delivered ultrasound-guided needle 30 can be inserted into a cyst 22, and can include apertures 32 and electrodes 34. Cyst 22 can include cyst fluid 24. Cyst fluid 24 can be a gas, liquid, semisolid substance, or mixed solid and cystic components.

Needle 30 can include an elongated shaft configured for passing through instrument channel 18 to interact with biological material. The needle shaft can define a lumen to allow fluid to pass through needle 30. In some cases, needle 30 can include a flow monitor and/or a pressure monitor on a distal end to regulate a rate and/or volume of fluid removed and/or injected into cyst 22. In some cases, needle 30 can have a gauge to monitor pressure within the cyst and regulate volume of injected fluid accordingly. In some cases, needle 30 can have a volumetric laser or light probe to pre-measure volume of injectate to be administered or administer light for targeted photodynamic therapy within the cyst therapy.

Apertures 32 can be defined by a distal end portion of needle 30. The needle 30 can be of different diameters compatible with endoscope 12, such as 25, 22, 19, and 18 French gauge. Apertures 32 can be used for aspiration of cyst fluid 24 through needle 30. In some cases, apertures 32 can additionally or alternatively be used to inject a fluid into cyst 22. In some cases, a volume of fluid injected via apertures 32 can be less than or substantially equal to a volume of cyst fluid 24 removed from cyst 22. In some cases, the injected fluid can be a conductive substance (e.g. saline or calcium chloride). In some cases, the injected fluid can conduct electric current to deliver irreversible non-contact electroporation and ablation to cyst 22. In some cases, the injected fluid can facilitate reversible electroporation by increasing the permeability of cells within cyst 22 such that a thereafter injected low dose chemotherapeutic or photosensitizer agent that can achieve chemoelectroablation or photodynamic ablation of cyst 22 using light. In some cases, a plurality of apertures 32 can be located on needle 30. In some cases, a single aperture 32 can be located on needle 30. In some cases, apertures 32 can be arranged linearly along needle 30. In some cases, apertures 32 can be arranged circumferentially around needle 30. In some cases, apertures 32 can be limited to one of aspiration or injection. In some cases, apertures 32 can perform both aspiration and injection.

One or more electrodes 34 on needle 30 can be used to produce an electrical field 36 through a conductive substance inside cyst 22. By creating electrical field 36, electrodes 34 can perform irreversible electroporation or reversible electroporation. In some cases, electrodes 34 can be uniformly spaced along the distal end of needle 30. In some cases, electrodes 34 can be variably spaced along the distal end of needle 30. In some cases, electrodes 34 can be monopolar or bipolar. In some cases, a polarity of electrodes 34 can be modified. In some cases, a polarity can be individually selected for each electrode 34. In some cases, electrodes 34 can be disabled. For example, if one electrode 34 is not located in cyst 22 when needle 30 is inserted, that electrode 34 can be disabled.

Figure 3:
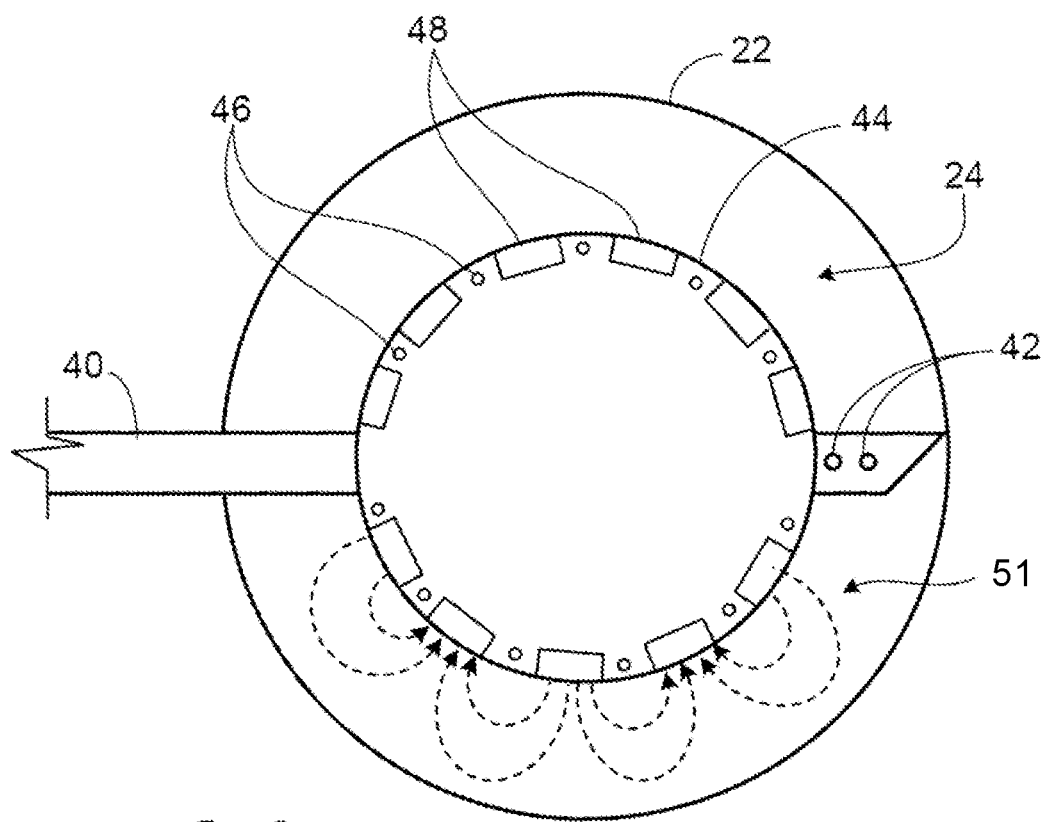
FIG. 3 is a schematic depiction of a second endoscopic ultrasound needle in a cyst in accordance with some embodiments provided herein.

Referring to FIG. 3, another embodiment of an endoscopically-delivered ultrasound-guided needle 40 can be inserted into a cyst 22, and can include aspiration and/or injection apertures 42 and a balloon 44. Balloon 44 can include injection or suction apertures 46 and electrodes 48. Cyst 22 can include cyst fluid 24. In some cases, cyst fluid 24 can be a gas, liquid, semisolid substance, or mixed solid and cystic components.

Needle 40 can include an elongated shaft configured for passing through instrument channel 18 to interact with biological material. The needle shaft can be of different diameters compatible with the endoscope 12, such as 25, 22, 19, and 18 French gauges. The needle shaft can define a lumen to allow fluid to pass through needle 40. In some cases, needle 40 can include a flow monitor and/or a pressure monitor on a distal end to regulate a rate and/or volume of fluid removed and/or injected into cyst 22. In some cases, needle 40 can have a gauge to monitor pressure within the cyst and regulate volume of injected fluid accordingly. In some cases, needle 40 can have a volumetric laser or light probe to pre-measure volume of injected fluid to be administered or administer light for targeted photodynamic therapy within the cyst therapy. Aspiration apertures 42 can be located at a distal end portion of needle 40. Aspiration apertures 42 can be used for aspiration of cyst fluid 24 through needle 40. In some cases, needle 40 can include a single aspiration aperture 42. In some cases, needle 40 can include a plurality of aspiration apertures 42. In some cases, aspiration apertures 42 can be arranged linearly along needle 40. In some cases, aspiration apertures 42 can be arranged circumferentially around needle 40.

Balloon 44 can be located a few millimeters (e.g., from about 5 mm to about 20 mm) from the distal end portion of needle 40. In some cases, balloon 44 can be made of composite material or polymer such as, but not limited to latex, silicon, duralon, or polyurethane. Balloon 44 can be inflated and deflated inside cyst 22. In some cases, balloon 44 can be inflated to have a diameter from about 5 mm to about 60 mm. In some cases, balloon 44 can take the shape, or a substantially similar shape, of cyst 22. In some cases, balloon 44 can be inflated such that a volume of balloon 44 can be less than or substantially equal to a volume of cyst fluid 24 removed. Balloon 44 can include injection apertures 46 and electrodes 48. Balloon 44 can be inflated using gas or liquid.

One or more injection apertures 46 defined by a wall of balloon 44 can inject a fluid (e.g., a solution) into cyst 22. In some cases, the injected fluid can cause inflation of balloon 44. In some cases, a volume of injected fluid can be less than or substantially equal to a volume of cyst fluid 24 removed from cyst 22. In some cases, the volume of the injected fluid into cyst 22 can be less than or substantially equal to the volume of cyst fluid 24 removed form cyst 22 less the volume of balloon 44 when inflated. In some cases, the injected fluid can be a conductive substance (e.g. saline or calcium chloride). In some cases, the injected fluid can conduct electric current to deliver irreversible non-contact electroporation and ablation to cyst 22. In some cases, the injected fluid can facilitate reversible electroporation by increasing the permeability of cells within cyst 22 such that a thereafter injected low dose chemotherapeutic or photosensitizer agent that can achieve chemoelectroablation or photodynamic ablation of cyst 22 using light.

In some cases, multiple injection and or suction apertures 46 can be located on balloon 44. In some cases, a single injection or suction aperture 46 can be located on balloon 44. In some cases, injection or suction apertures 46 can be located around a single cross sectional circumference of balloon 44. In some cases, injection or suction apertures 46 can be located around multiple cross sectional circumferences of balloon 44. In some cases, the cross section circumference(s) can be parallel or perpendicular to needle 40. In some cases, injection or suction apertures 46 can be uniformly distributed around the surface of balloon 44. In some cases, injection or suction apertures 46 can be variously distributed around the surface of balloon 44.

One or more electrodes 48 coupled to an outer surface of the wall of balloon 44 can be used to produce an electrical field 50 through a conductive substance inside cyst 22. In some cases, multiple electrodes 48 can be located on balloon 44. In some cases, electrodes 48 can be located between injection apertures 46. In some cases, a single electrode 48 can be located on balloon 44. In some cases, electrodes 48 can be located around a single cross sectional circumference of balloon 44. In some cases, electrodes 48 can be located around multiple cross sectional circumferences of balloon 44. In some cases, electrodes 48 can be located around the same cross sectional circumferences of balloon 44 as injection apertures 46. In some cases, electrodes 48 can be located around different cross sectional circumferences of balloon 44 as injection apertures 46. In some cases, the cross section circumference(s) can be parallel or perpendicular to needle 40. In some cases, electrodes 48 can be uniformly distributed around the surface of balloon 44. In some cases, electrodes 48 can be variously distributed around the surface of balloon 44. In some cases, electrodes 48 can be monopolar or bipolar. In some cases, a polarity of electrodes 48 can be modified. In some cases, a polarity can be individually selected for each electrode 48.

Figure 4:
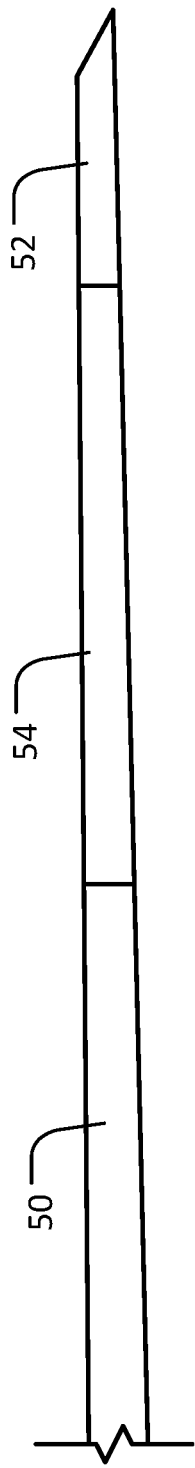
FIG. 4 is a schematic depiction of a third endoscopic ultrasound needle in a first configuration in accordance with some embodiments provided herein.
Figure 5:
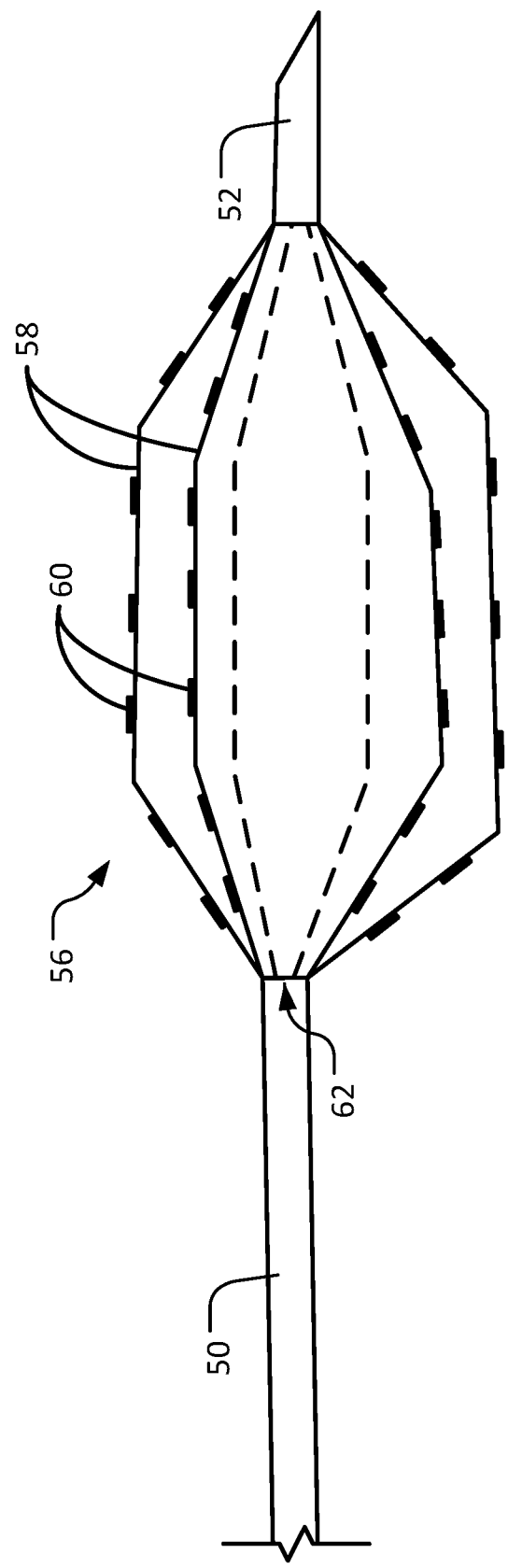
FIG. 5 is a schematic depiction of the third endoscopic ultrasound needle of FIG. 4 in a second configuration in accordance with some embodiments provided herein.

Referring to FIGS. 4 and 5, another embodiment of an endoscopically-delivered ultrasound-guided needle 50 can be inserted into a cyst (not shown), and can include a sheath 54 covering an electroporation basket 56 located proximal of a needle tip portion 52 of the needle 50. Electroporation basket 56 can include one or more arms 58 and one or more electrodes 60 disposed on each of the arms 58. Cysts can include a cyst fluid. In some cases, the cyst fluid can be a gas, liquid, semisolid substance, or mixed solid and cystic components.

Needle 50 can include an elongated shaft configured for passing through instrument channel 18 to interact with biological material. The needle shaft can be of different diameters compatible with the endoscope 12, such as 25, 22, 19, and 18 French gauges. The needle shaft can define a lumen to allow fluid to pass through needle 50. In some cases, needle 50 can include a flow monitor and/or a pressure monitor on a distal end portion to regulate a rate and/or volume of fluid removed and/or injected into the cyst. In some cases, needle 50 can have a gauge to monitor pressure within the cyst and regulate volume of injected fluid accordingly. In some cases, needle 50 can have a volumetric laser or light probe to pre-measure volume of injected fluid to be administered, or to administer light for targeted photodynamic therapy within the cyst therapy.

An aspiration/injection port can be located at a distal portion 62 of needle 50. Aspiration/injection ports can be used for aspiration of cyst fluid through needle 50. In some cases, needle 50 can include a single aspiration/injection port. In some cases, needle 50 can include a plurality of aspiration/injection ports. In some cases, two or more aspiration/injection ports can be arranged linearly along needle 50. In some cases, two or more aspiration/injection ports can be arranged circumferentially around needle 50. In some cases, an aspiration/injection port can be located on an end of needle 50 proximal of electroporation basket 56. In some cases, needle 50 can be delivered to the targeted structure (e.g., a cyst, or other structure) over a guide wire.

The aspiration/injection port can be used to remove fluid from the cyst. In some embodiments, the aspiration/injection port can also be used to inject a fluid (e.g., a solution) into the cyst. In some cases, a volume of injected fluid can be less than or substantially equal to a volume of cyst fluid removed from the cyst. In some cases, the injected fluid can be a conductive substance (e.g., saline or calcium chloride). In some cases, the injected fluid can be used to conduct electric current to deliver irreversible non-contact electroporation and/or ablation to the cyst. In some cases, the injected fluid can facilitate reversible electroporation by increasing the permeability of cells within the cyst such that a thereafter-injected low dose chemotherapeutic or photosensitizer agent can faciliate chemoelectroablation or photodynamic ablation of the cyst using light. In some cases, the fluid injected through the aspiration/injection port can be a chemotherapeutic, chemical, ablative, or immunological substance to enhance the electroporation ablative effect.

Electroporation basket 56 can be located a few millimeters (e.g., from about 5 mm to about 20 mm) from needle tip portion 52. Electroporation basket 56 can be flexible and can expand to an open configuration (e.g., as shown in FIG. 5) once sheath 54 is removed. In some cases, electroporation basket 56 can expand to have a diameter from about 5 mm to about 60 mm. In some cases, electroporation basket 56 can take the shape, or a substantially similar shape, of the cyst. In some cases, arms 58 can expand independently to conform to the shape and size of the targeted structure (e.g., the cyst), such that electrodes 60 are in close proximity to the wall of the cyst. In some cases, the cyst can be aspirated or vacuum can be applied, to better approximate the cyst wall to electrodes 60 of electroporation basket 56.

One or more electrodes 60 coupled to arms 58 of electroporation basket 56 can be used to produce an electrical field through a conductive substance inside the cyst. In some cases, multiple electrodes 60 can be located on each of arms 58. In some cases, a single electrode 60 can be located on each of arms 58. In some cases, multiple electrodes 60 can be located around a single cross section of electroporation basket 56. In some cases, electrodes 60 can be located around multiple cross section of electroporation basket 56. In some cases, the cross sections can be parallel or perpendicular to needle 50. In some cases, electrodes 60 can be uniformly distributed around electroporation basket 56. In some cases, electrodes 60 can be variously distributed around electroporation basket 56. In some cases, electrodes 60 can be monopolar or bipolar. In some cases, the polarity of electrodes 60 can be modified as desired. In some cases, the polarity can be individually selected for each electrode 60.

In some cases, electroporation can be delivered by creating an electrical field with the electrodes 60 in contact with the cyst. In some cases, electroporation can be delivered by creating an electrical field without the electrodes 60 in contact with the cyst, via a conductive solution injected via the needle 50 into the cyst. In some cases, the electrical field (e.g., DC pulses, RF energy, etc.) can be unipolar or bipolar in nature with the cathode and anode on the electroporation basket 56. In some cases, the duration and depth of the treatment effect can be regulated by electrical impedance sensors located on or near to the electroporation basket 56 that measure the opposition that a circuit presents to a current when a voltage is applied. In some cases, the applied current can be unipolar with a return electrode inserted via endoscopic ultrasound in a structure adjacent to the targeted structure (e.g., such as the mesentery, perigastric, or periduadenal space). Such a configuration of the endoscopic ultrasound electroporation needle can be used to apply an electroporation electrical field to structures such as pancreas cystic lesions, bile duct, pancreas duct, visceral fat pads (e.g., at the level of the celiac mesentery), celiac ganglia, liver or pancreas lesions, without limitation.

Once the treatment is delivered, electroporation basket 56 can be covered by sheath 54 to radially reduce its size, and needle 50 can be withdrawn from the targeted structure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. An endoscopically-deliverable ultrasound-guided electroporation needle, the needle comprising:
    a single elongate needle shaft defining a longitudinal axis and configured to be slidably disposed within a working channel of an endoscope that includes an ultrasound head located at a distal end of the endoscope;
    a first aperture defined at a distal end portion of the needle shaft, the first aperture configured to aspirate a first fluid through a lumen defined by the elongate needle shaft;
    a second aperture defined by the distal end portion of the needle shaft and arranged linearly with respect to the first aperture longitudinally along the needle shaft, the second aperture configured to inject a second fluid through the lumen; and
    three electrodes arranged on the needle shaft proximal of the distal end portion of the needle shaft, wherein the three electrodes are longitudinally spaced apart from each other along the needle shaft and are configured to simultaneously generate two separate electrical fields in the second fluid,
    wherein the needle shaft, including the portion of the needle shaft on which the three electrodes are arranged, is configured for insertion into a cystic structure such that the three electrodes are positioned within the cystic structure, and
    wherein the distal end portion of the needle shaft is free of any electrodes.

2. The needle of claim 1, further comprising at least one of a flow monitor and a pressure monitor in communication with a lumen defined by the needle shaft.

3. The needle of claim 1, wherein a tip of the needle is blunt and the needle is configured to be delivered over a wire into the cystic structure.

4. The needle of claim 1, wherein the first aperture is configured to inject the first fluid, and the second aperture is configured to aspirate the second fluid.

5. The needle of claim 1, further comprising a gauge configured to monitor pressure within a cystic structure and regulate a volume of an injected fluid.

6. The needle of claim 1, further comprising a volumetric light probe configured to pre-measure a volume of a fluid to be injected.

7. The needle of claim 6, wherein the volumetric light probe is configured to administer light to a cystic structure as part of a targeted photodynamic therapy.

8. The needle of claim 7, wherein the volumetric light probe is a volumetric laser.

9. The needle of claim 1, wherein, upon injection, the second fluid is configured to conduct an electric current to deliver irreversible non-contact electroporation and ablation to a cystic structure.

10. The needle of claim 1, wherein, upon injection, the second fluid is configured to conduct an electric current to deliver reversible electroporation.

11. The needle of claim 1, wherein each of the three electrodes is configured to be selectively disabled.

12. An endoscopically-deliverable ultrasound-guided electroporation needle, the needle comprising:
- a single elongate needle shaft defining a longitudinal axis and configured to be slidably disposed within a working channel of an endoscope that includes an ultrasound head located at a distal end of the endoscope;
- a first aperture defined at a distal end portion of the needle shaft, the first aperture configured to aspirate a first fluid through a lumen defined by the elongate needle shaft;
- a second aperture defined by the distal end portion of the needle shaft, the second aperture configured to inject a second fluid through the lumen; and
- three electrodes arranged on the needle shaft proximal of the distal end portion of the needle shaft, wherein the three electrodes are longitudinally spaced apart from each other along the needle shaft and are configured to simultaneously generate two separate electrical fields in the second fluid,
- wherein the first and second apertures are arranged circumferentially around the needle shaft at a same longitudinal distance from a tip of the needle shaft,
- wherein the needle shaft, including the portion of the needle shaft on which the three electrodes are arranged, is configured for insertion into a cystic structure such that the three electrodes are positioned within the cystic structure, and
- wherein the distal end portion of the needle shaft is free of any electrodes.

13. The needle of claim 12, wherein each of the three electrodes is configured to be selectively disabled.

14. An endoscopically-deliverable ultrasound-guided electroporation needle system, the electroporation needle system comprising:
- an endoscope comprising an ultrasound head located at a distal end thereof, the endoscope defining a working channel with an outlet at the distal end of the endoscope;
- a single elongate needle shaft defining a longitudinal axis and slidably disposable within the working channel of the endoscope;
- a first aperture defined at a distal end portion of the needle shaft, the first aperture configured to aspirate a first fluid through a lumen defined by the elongate needle shaft;
- a second aperture defined by the distal end portion of the needle shaft and arranged linearly with respect to the first aperture longitudinally along the needle shaft, the second aperture configured to inject a second fluid through the lumen; and
- three electrodes arranged on the needle shaft proximal of the distal end portion of the needle shaft, wherein the three electrodes are longitudinally spaced apart from each other along the needle shaft and are configured to simultaneously generate two separate electrical fields in the second fluid,
- wherein the needle shaft, including the portion of the needle shaft on which the three electrodes are arranged, is configured for insertion into a cystic structure such that the three electrodes are positioned within the cystic structure, and
- wherein the distal end portion of the needle shaft is free of any electrodes.

15. The electroporation needle system of claim 14, wherein the ultrasound head is disposed above the outlet of the working channel.

16. The electroporation needle system of claim 14, wherein each of the three electrodes is configured to be selectively disabled.

* * * * *